(12) United States Patent
Lentz

(10) Patent No.: US 7,959,660 B2
(45) Date of Patent: Jun. 14, 2011

(54) MULTIFILAR CABLE CATHETER

(75) Inventor: David Christian Lentz, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 292 days.

(21) Appl. No.: 11/300,635

(22) Filed: Dec. 14, 2005

(65) Prior Publication Data

US 2006/0142704 A1    Jun. 29, 2006

Related U.S. Application Data

(60) Provisional application No. 60/636,192, filed on Dec. 15, 2004.

(51) Int. Cl.
  *A61F 2/06*    (2006.01)
  *A61M 29/00*   (2006.01)
  *A61M 5/00*    (2006.01)

(52) U.S. Cl. .................. 623/1.11; 606/192; 604/264

(58) Field of Classification Search ............... 604/103.9, 604/264, 524–527; 623/1.11; 606/191, 192
See application file for complete search history.

(56) References Cited

U.S. PATENT DOCUMENTS

| | | | |
|---|---|---|---|
| 4,362,150 A | | 12/1982 | Lombardi, Jr. et al. |
| 4,660,571 A | * | 4/1987 | Hess et al. .................... 607/116 |
| 4,762,129 A | | 8/1988 | Bonzel |
| 4,906,241 A | * | 3/1990 | Noddin et al. ................ 606/194 |
| 4,917,104 A | * | 4/1990 | Rebell ........................... 600/585 |
| 4,960,410 A | | 10/1990 | Pinchuk |
| 4,976,720 A | * | 12/1990 | Machold et al. .............. 606/194 |
| 4,998,923 A | | 3/1991 | Samson et al. |
| 5,295,962 A | * | 3/1994 | Crocker et al. .......... 604/101.02 |
| 5,346,505 A | * | 9/1994 | Leopold ........................ 606/194 |
| 5,425,711 A | | 6/1995 | Ressemann et al. |
| 5,429,597 A | * | 7/1995 | DeMello et al. .............. 604/509 |
| 5,507,768 A | | 4/1996 | Lau et al. |
| 5,507,995 A | | 4/1996 | Schweich, Jr. et al. |
| 5,533,968 A | * | 7/1996 | Muni et al. ............... 604/103.11 |
| 5,643,278 A | | 7/1997 | Wijay et al. |
| 5,690,644 A | | 11/1997 | Yurek et al. |
| 5,695,468 A | | 12/1997 | Lafontaine et al. |
| 5,711,909 A | | 1/1998 | Gore et al. |
| 5,728,067 A | | 3/1998 | Enger |
| 5,906,606 A | * | 5/1999 | Chee et al. .................... 604/527 |
| 5,932,035 A | * | 8/1999 | Koger et al. ................... 148/563 |
| 5,938,587 A | | 8/1999 | Taylor et al. |

(Continued)

FOREIGN PATENT DOCUMENTS

EP          1374943        1/2004

(Continued)

OTHER PUBLICATIONS

International Search Report and Written opinion from related PCT App. No. PCT/US2005/045282—(Dec. 14, 2005).

(Continued)

*Primary Examiner* — Theodore J Stigell
*Assistant Examiner* — William Carpenter
(74) *Attorney, Agent, or Firm* — Brinks Hofer Gilson & Lione

(57) ABSTRACT

A catheter device including an elongate catheter shaft comprising a multifilar cable tubing having a proximal portion and a distal portion. At least a part of the distal portion is more flexible than the proximal portion.

5 Claims, 8 Drawing Sheets

U.S. PATENT DOCUMENTS

| | | | |
|---|---|---|---|
| 5,941,869 A * | 8/1999 | Patterson et al. | 604/508 |
| 6,030,405 A | 2/2000 | Zarbanty et al. | |
| 6,102,890 A | 8/2000 | Stivland et al. | |
| 6,107,004 A | 8/2000 | Donadio, III | |
| 6,186,978 B1 * | 2/2001 | Samson et al. | 604/96.01 |
| 6,346,092 B1 | 2/2002 | Leschinsky | |
| 6,548,010 B1 * | 4/2003 | Stivland et al. | 264/482 |
| 6,589,227 B2 * | 7/2003 | Sønderskov Klint | 604/524 |
| 6,629,952 B1 | 10/2003 | Chien et al. | |
| 6,648,854 B1 | 11/2003 | Patterson et al. | |
| 6,692,460 B1 * | 2/2004 | Jayaraman | 604/102.02 |
| 7,025,758 B2 | 4/2006 | Klint | |
| 7,037,291 B2 | 5/2006 | Lee et al. | |
| 7,306,585 B2 | 12/2007 | Ross | |
| 2002/0099405 A1 | 7/2002 | Yurek et al. | |
| 2003/0105427 A1 * | 6/2003 | Lee et al. | 604/103.04 |
| 2004/0010243 A1 * | 1/2004 | Klint | 604/526 |
| 2004/0116833 A1 | 6/2004 | Kato et al. | |
| 2004/0133158 A1 | 7/2004 | Keith et al. | |
| 2005/0283221 A1 | 12/2005 | Mann et al. | |
| 2006/0259118 A1 | 11/2006 | Pal et al. | |
| 2008/0097398 A1 | 4/2008 | Mitelberg et al. | |

FOREIGN PATENT DOCUMENTS

| | | |
|---|---|---|
| WO | WO93/04722 | 3/1993 |
| WO | WO98/44981 | 10/1998 |
| WO | WO2006/107919 | 10/2006 |

OTHER PUBLICATIONS

Creganna Medical Devices brochure, 2004, 14 pages.
International Search Report and Written Opinion from PCT Application No. PCT/US2006/012424, filed Apr. 4, 2006.
Meredith, Ian T., Driver™ Stent Experience, Dec. 2003, 18 pages.
Complete file history, including Office Actions, of U.S. Appl. No. 11/748,906, filed May 15, 2007 by Lentz, David Christian.

* cited by examiner

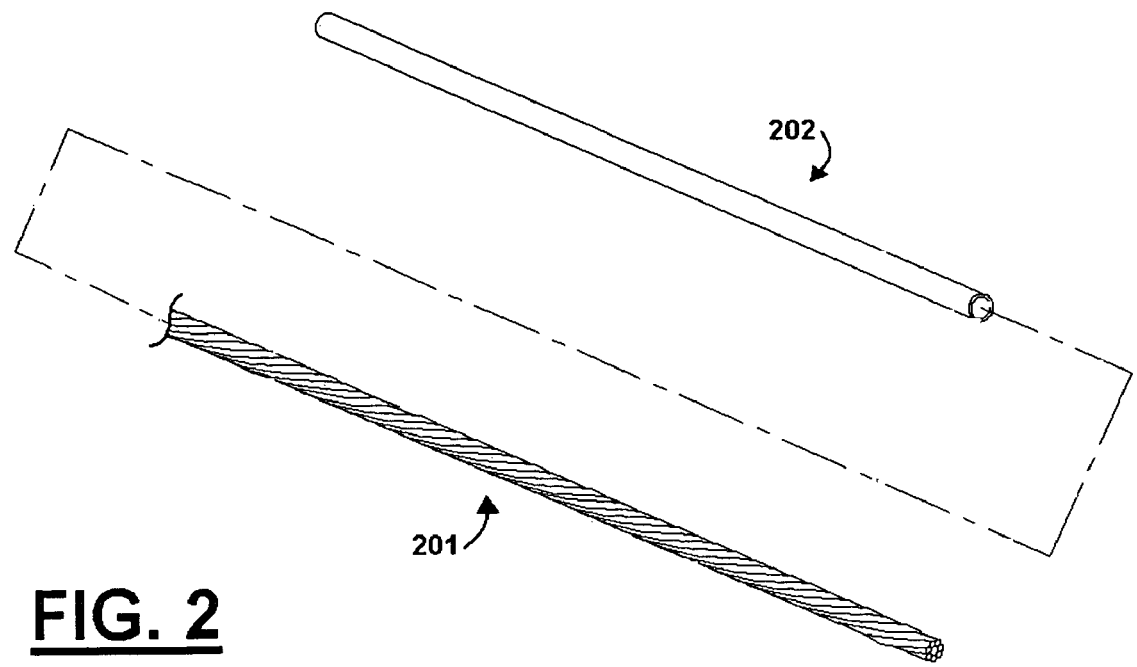
FIG. 2
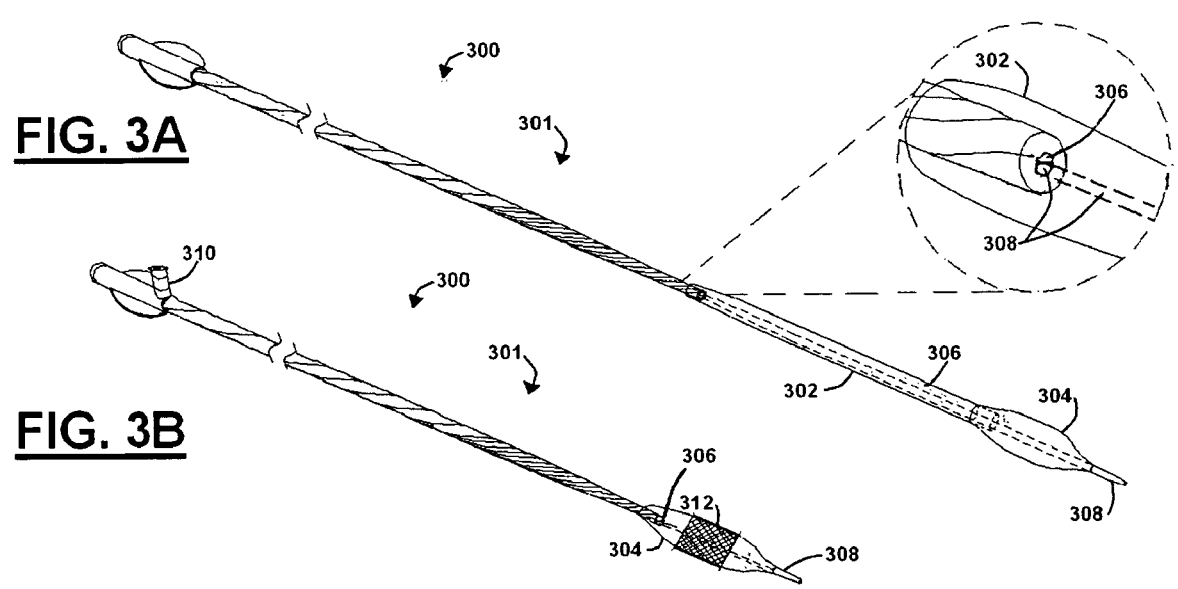
FIG. 3A
FIG. 3B

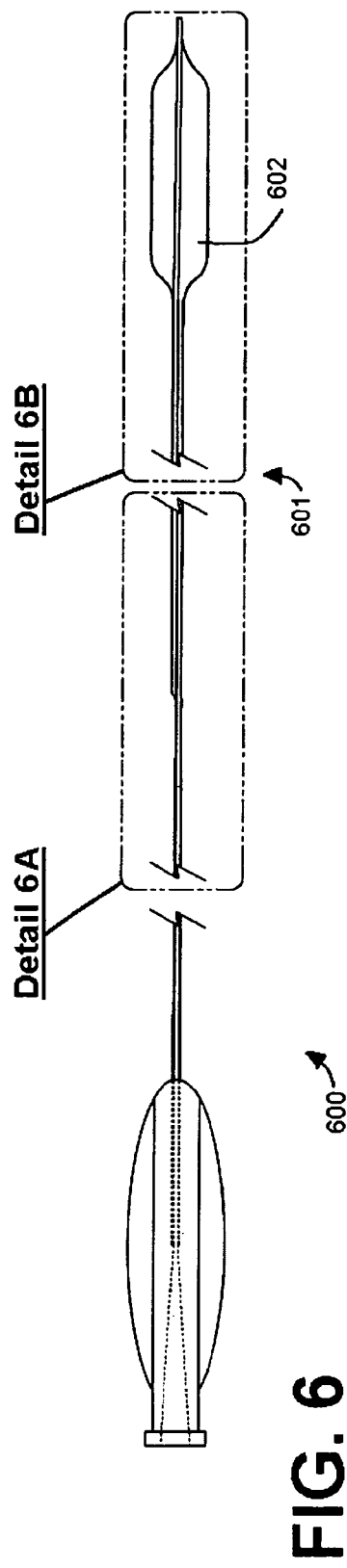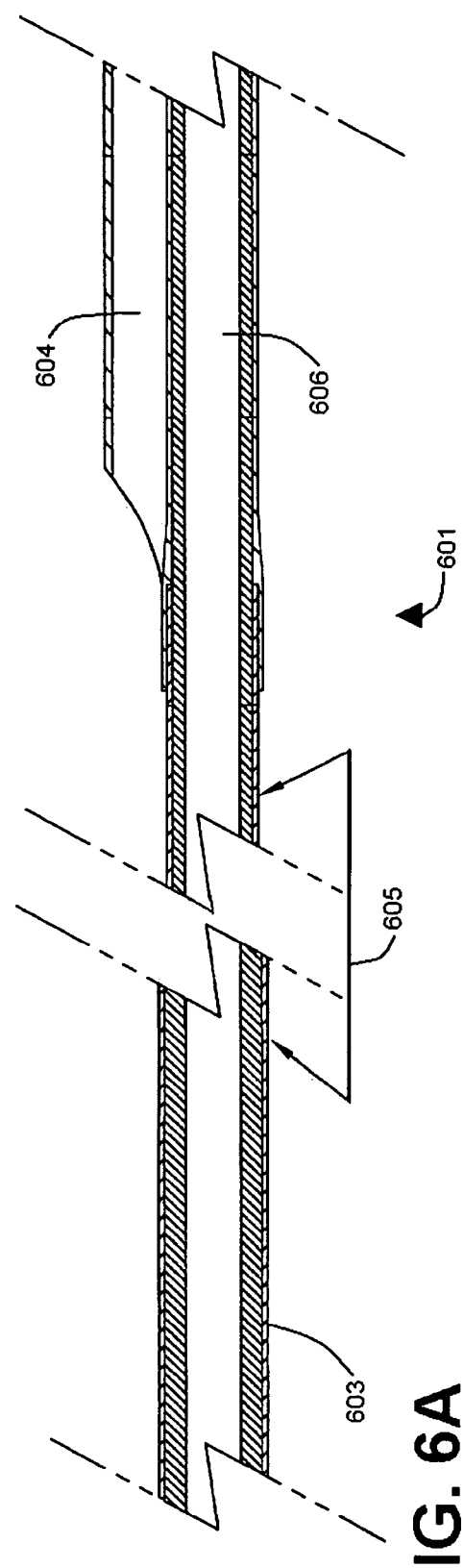

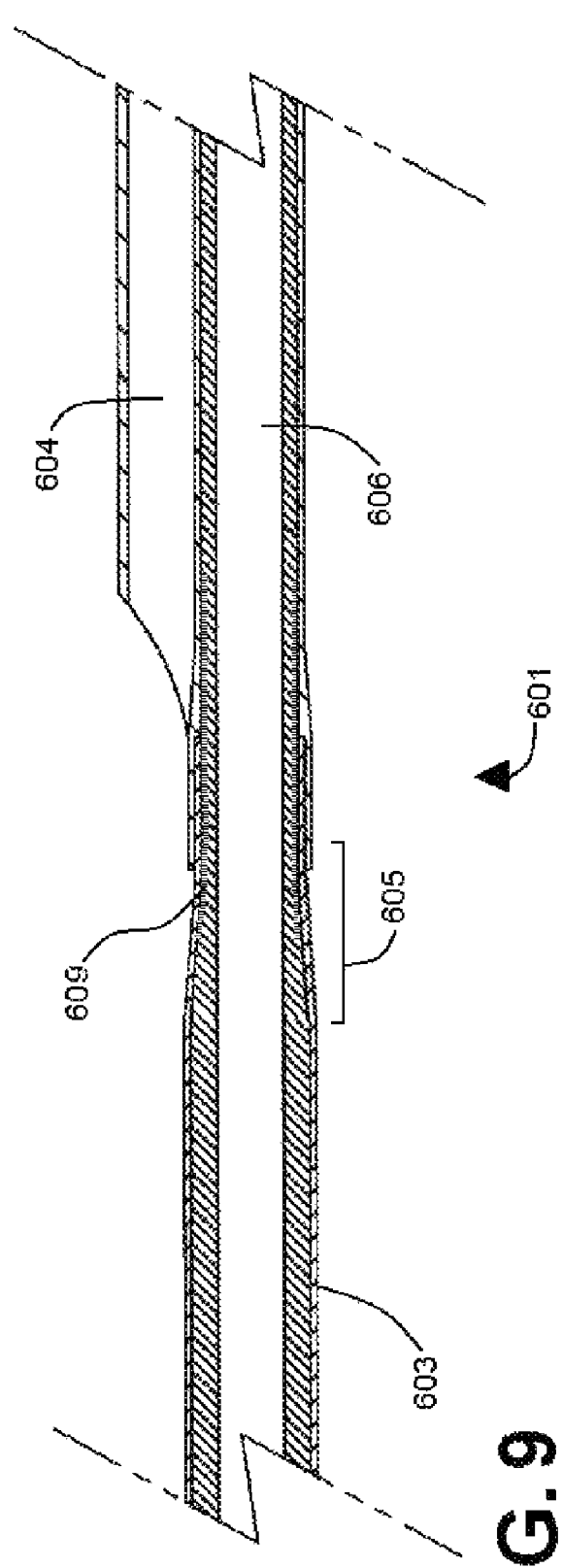

# MULTIFILAR CABLE CATHETER

CROSS-REFERENCE TO RELATED APPLICATIONS

This application claims priority to U.S. Provisional Application Ser. No. 60/636,192, filed Dec. 15, 2004.

TECHNICAL FIELD

The present application relates to medical catheters, and more specifically to medical catheters useful in endovascular and other body lumens.

BACKGROUND

Medical delivery catheters are well known in the art of minimally invasive surgery for introduction of fluids and devices to sites inside a patient's body. For example, balloon dilation of luminal stenoses (e.g., in procedures such as angioplasty or balloon dilation of a bile duct), stent placement, and introduction of radio-opaque contrast fluids are common uses of catheters.

The most widely used form of angioplasty makes use of a dilation catheter having an inflatable balloon at its distal end. In coronary procedures, a hollow guide catheter or wire guide typically is used for guiding the dilation catheter through the vascular system to a position near the stenosis (e.g., to a coronary arterial lumen occluded by plaque). Using fluoroscopy, the physician guides the dilation catheter the remaining distance through the vascular system until a balloon is positioned to cross the stenosis. The balloon is then inflated by supplying pressurized fluid, through an inflation lumen in the catheter, to the balloon. Inflation of the balloon causes a widening of the lumen of the artery to reestablish acceptable blood flow through the artery. In some cases, a stent may be deployed with or instead of the balloon to widen and hold open the occluded arterial lumen.

Preferably a catheter used in endovascular lumens will have several physical characteristics. The profile and shaft size of the dilation catheter should be such that the catheter can reach and cross a very tight stenosis. Portions of the dilation catheter must also be sufficiently flexible to pass through a tight curvature or tortuous passageway, especially in a catheter adapted for use in the coronary arteries. The ability of a catheter to bend and advance effectively through the endovascular or other lumens is commonly referred to as the "trackability of the catheter." Another important feature of a dilation catheter is its "pushability." Pushability involves the transmission of longitudinal forces along the catheter from its proximal end to its distal end so that a physician can push the catheter through the vascular or other lumenal system and the stenoses. Effective catheters should be both trackable and pushable.

Two commonly used types of dilation catheters are referred to as "long-wire" catheters and "short-wire" catheters. A long-wire catheter is one in which a wire guide lumen is provided through the length of the catheter that is adapted for use with a wire guide that can first be used to establish the path to and through a stenosis to be dilated. The dilation catheter can then be advanced over the wire guide until the balloon on the catheter is positioned within the stenosis.

In short-wire catheters, the wire guide lumen may not extend the entire length of the catheter. In this type of catheter, the wire guide lumen may extend only from the distal end of the balloon to a point intermediate the distal and proximal ends of the catheter. This shorter lumen is the only portion of the catheter contacting the wire guide. It is sometimes desirable to exchange this first catheter and/or balloon for a second catheter (e.g., to "exchange out" a balloon catheter, and then "exchange in" a stent-deployment catheter). The exchange is preferably executed by leaving the wire guide in place during removal of the first catheter and using it as a guide for the second catheter. The first catheter is withdrawn or otherwise removed over the wire guide, and then a second catheter is introduced over the wire guide.

Short-wire catheters are often easier to exchange than catheters having the wire guide lumen extending the entire length of the catheter. This is because the wire guide need not be as long as a "long wire" configuration, which requires that a length of the wire guide extending outside the patient's body be longer than the portion of the catheter extending over the long wire guide in order for a doctor or assistant to maintain a grasp on the wire guide (to avoid undesired movement or displacement thereof). The short wire guide configuration catheters also create less friction during mounting and exchange operations due to the shorter wire guide lumen, leading to a reduced likelihood of displacing the wire guide.

Catheters for use in endovascular lumens typically require a variation in physical properties along different portions thereof. For example, a certain degree of stiffness is required for pushability and trackability near the proximal end while distal end requires a great deal of flexibility. A catheter having uniform properties throughout its length poses disadvantages in that it is likely to be too proximally flexible or too distally stiff. As a result, most catheter shafts (especially endovascular catheters) are made from multiple materials along the shaft length. For example, a catheter shaft may have a stiff proximal portion made of metal hypotube, a middle portion made of a stiff plastic, and a distal portion made of a more flexible plastic. This combination of materials poses problems of cost and efficiency in construction, and the junctions provide problematic possibilities for structural failure (such as binding, kinking, or even separation) as well as requiring specialized connection means. In another example, a catheter shaft may be made of plastic for a major part of its length, but have a stiffening wire disposed through a significant portion of that length to enhance stiffness. Some long wire catheters rely almost wholly on placement of a wire guide therethrough to retain the needed stiffness, which presents the problems of length and unwieldiness discussed above. In contrast, the proximal sections of short wire catheters must have adequate stiffness independent of the wire guide.

Several different structures for shortened guide wire lumen dilation catheters have been proposed and used to obtain the desired physical properties described above, but each of these structures tends to suffer from several disadvantages. For example, in a short wire catheter having a relatively flexible one-piece plastic design, because only a small portion of the wire guide extends through the catheter body near the distal end of the catheter shaft, the wire guide portion does not contribute to the pushability of the rest of the catheter shaft. As a result, the proximal shaft portion of such a catheter has low column strength. With such a configuration, the shafts and guide wire may tend to develop undesirable flexure (e.g., scissoring, bowing, buckling, kinking) when the balloon is being manipulated in a lumen. This undesired flexure may cause an irregular exterior surface such as a sharp edge which can in turn cause injurious abrasions to the inner lining of the artery or other lumen (e.g. other body lumen or a working lumen of an endoscope). This undesired flexure also leads to poor pushability and trackability of the catheter. To counteract this deficiency, some known designs have extended the length of the wire guide lumen and/or provided additional stiffener elements in the shaft.

In one design, a significant proximal portion of the catheter shaft is made of a metallic tubing (commonly referred to as a hypotube), which provides the desired pushability while maintaining a relatively small outer diameter. The distal portion of the catheter shaft is a second, more flexible (commonly plastic) tubing. In short-wire catheters using the hypotube design, a first aperture for introduction of a wire guide to the wire guide lumen is usually placed in the hypotube near to the distal end thereof. Alternatively, this first aperture is placed in the second tubing, or near the juncture between the hypotube and second tubing. These types of catheters, however, present certain disadvantages. Having the first aperture in the hypotube mitigates the advantages of a short-wire catheter: the wire guide must be longer, and advantages conferred by reduced friction are lessened. Having the first aperture at the aforementioned juncture or in the second tubing creates a likelihood of undesired flexure (e.g., kinking or bunching) as there will be at least some portion of the more flexible second tubing unsupported by a wire guide, and therefore lacking column strength. Not only may such undesired flexure injure an endovascular or other lumen housing the catheter, but it may close off an inflation lumen or other lumen of the catheter, which is undesirable. The problems of increased cost of assembly and various mechanical problems presented by constructing and using a catheter having both semi-flexible hypotube and more flexible second tubing portions of the same catheter are addressed in the present invention.

BRIEF SUMMARY

The present invention provides a catheter device, adaptable for use in endovascular lumens or other body lumens, that has a construction of multifilar cable tubing for a substantial portion of its length and that is adaptable for use in a short-wire or long-wire configuration. The embodiments described and claimed herein provide a catheter shaft having good pushability and trackability. Embodiments of the present invention are adaptable for a variety of applications (e.g., placement of expandable stents, balloon dilation of stenoses) and use in a variety of surgical locations (e.g., vascular, gastroenterological).

The embodiments herein are adaptable for use in a variety of minimally invasive surgical treatments (including, e.g., angioplasty or bile duct dilation).

BRIEF DESCRIPTION OF THE DRAWINGS

FIG. 2 is a perspective view of a catheter shaft with a sleeve;

FIG. 3A is a perspective view of a catheter device having a distal extension and an inflation balloon, with an enlarged detail view of the features at the catheter's distal end;

FIG. 3B is a perspective view of a catheter device with an inflation balloon;

FIG. 6 is a side view of a tapered catheter device having an external distal wire guide lumen structure and an inflation balloon;

FIG. 6A is a detail of FIG. 6 and shows a longitudinal cross-sectional view of the tapering portion and external wire guide lumen of a catheter device;

FIG. 6B is a detail of FIG. 6 and shows a longitudinal cross-sectional view of the distal portion of the catheter device, with an enlarged detail view of features where the catheter shaft meets the balloon;

FIG. 9 provides a longitudinal section view of an alternatively embodied portion of the catheter shown in FIGS. 6-6D, including an inner coating segment.

DETAILED DESCRIPTION

The presently described embodiments of a multifilar tube catheter shaft are adaptable for use in a variety of minimally invasive surgical applications (e.g. endoscopic procedures, angioplasty).

Figure 1A:
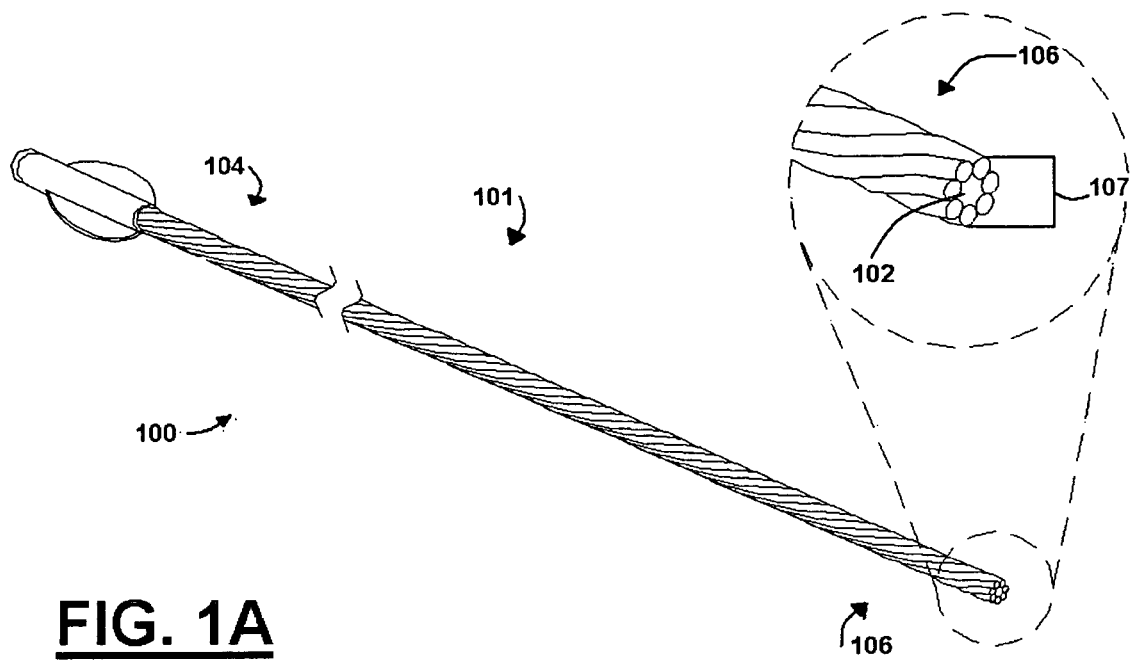
FIG. 1A is a perspective view of a catheter, with an enlarged detail view of the catheter's distal end.
Figure 1B:
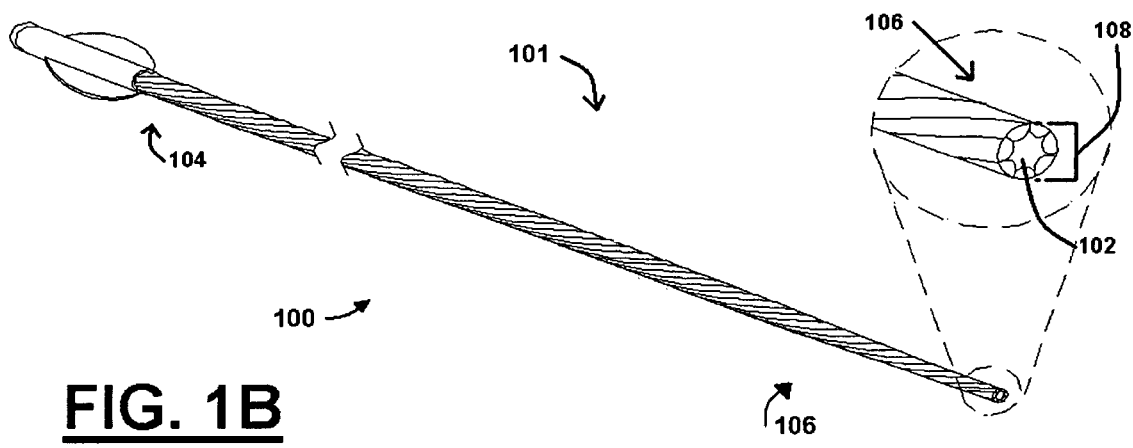
FIG. 1B is a perspective view of a tapered catheter device, with an enlarged detail view of the catheter's distal end.

FIGS. 1A-1B illustrate an embodiment of a catheter device 100 with a shaft 101 constructed of a multifilar material and having an internal lumen 102. The multifilar tubing described is made of a plurality of wires twisted together and leaving a central lumen. Such multifilar tubing may be obtained, for example, from Asahi-Intecc (Newport Beach, Calif.). Materials and methods of manufacturing a suitable multifilar tubing are described in Published U.S. Pat. App. 2004/0116833 (Koto et al.), the contents of which are incorporated herein by reference. Use of multifilar tubing in a vascular catheter device is described in U.S. Pat. No. 6,589,227 (Sonderskov Klint, et al.; Assigned to Cook Inc. of Bloomington, Ind. and William Cook Europe of Bjaeverskov, Denmark), which is also incorporated herein by reference.

In FIG. 1A, the exterior diameter 107 is approximately the same along the length of the shaft 101. In the embodiment shown in FIG. 1B, the proximal end 104 has a greater exterior diameter than the distal end 106. The catheter shaft 101 tapers toward a smaller exterior diameter 108 at the distal end 106. Tapering can enhance flexibility of the shaft 101 in several ways. For example, flexibility is enhanced by decreasing the outside diameter of the catheter shaft 101. The portion of the catheter shaft 101 having a smaller diameter is more flexible than the portion having a larger diameter. Such tapering also decreases the thickness of the wall of the catheter shaft 101. Alternatively, tapering may be used within the internal diameter of a catheter, enhancing flexibility by decreasing wall thickness without altering the exterior diameter of the shaft 101. The steepness and location of the tapering is determined by the desired application for the catheter shaft 101. For example, in alternative embodiments, there may be multiple stepwise or gradual differences in diameter to confer different degrees of flexibility throughout the length of the catheter. For example, catheter shaft 101 for use in coronary arteries will typically benefit from a smaller diameter than a catheter shaft 101 for use in a bile duct, both for gross size and flexibility. A grinding process or other suitable process may be used to reduce the exterior diameter as appropriate for the desired application. Reducing the exterior diameter provides an added benefit by reducing the profile of the device. The flexibility of the catheter shaft 101 or a portion thereof may also be altered by increasing or decreasing the number of filars. In one aspect, the embodiments described herein also provide a catheter shaft having consistent construction material throughout most of the length of the catheter shaft, with gradual transition from a stiffer proximal end to a more flexible distal end and lacking sharp transitions that undermine structural integrity.

A further embodiment of the catheter shaft 101 includes a coating on internal and/or external surfaces for at least a portion of the catheter shaft 101. The coating is selected to confer or improve one or more properties of reduced friction, flexibility, and sealing a lumen 102 of the catheter. Sealing the lumen 102 allows the lumen to be used, for example, for introduction of inflation fluid to a dilation balloon or introduction of a medicative substance or radio-opaque contrast fluid.

The coating may be, for example, a sheath or sleeve 202 as illustrated in FIG. 2. In various alternative embodiments, the sheath 202 may comprise an extruded sleeve, shrink tube, extruded over-jacket, or dip coat. The sheath 202 is preferably a thermoset material or a thermoplastic material and may comprise, for example, HDPE, PTFE, PEBA, PET, polyurethane, polyimide, polyolefin, nylon, or any combination thereof. The coating may be applied by, for example, over-extrusion, dip-coating, melt fusion, or heat shrinking. For example, PET shrink tube 202 has the advantage of providing an increased stiffness to a small diameter catheter shaft 201. On the other hand, a PEBA (Polyether Block Amide) shrink tube 202 can be used with a larger diameter catheter shaft 201 where greater flexibility is desired. The type of sleeve 202 material may also be selected to complement other catheter components; for example, a nylon sleeve 202 may bond and interact better with a nylon expandable member such as a balloon or basket and/or a nylon wire guide lumen. Selection of coating materials, filar size and number, and diameter allow manipulation of the catheter shaft's 201 shore hardness to offer the desired functional properties.

FIGS. 3A-3B illustrate embodiments of balloon catheters 300 comprising a multifilar shaft 301. In the embodiment of FIG. 3A, the catheter shaft 301 has a distal extension 302, upon which is mounted an inflation balloon 304. The distal extension 302 can be formed of the same group of materials used in the coating (HDPE, PTFE, PEBA, PET, polyurethane, polyimide, polyolefin, nylon, or any combination thereof) and provides a shaft portion that may be more flexible than the shaft 301. As can clearly be seen in the detail illustration portion of FIG. 3A, the extension 302 encloses an inflation lumen 306 which continues from an inflation lumen 306 of the multifilar catheter shaft 301. The extension 302 also encloses a wire guide lumen 308. In the illustrated long wire configuration catheter 300, the wire guide lumen extends from the proximal end of the multifilar catheter shaft 301 and extends through the inflation balloon 304 at the distal end.

The embodiment illustrated in FIG. 3B has an inflation balloon 304 disposed directly on the distal end of the catheter shaft 301. An inflation lumen 306 of the multifilar catheter shaft 301 opens into the inflation balloon 304. A wire guide lumen 308 traverses the interior of the balloon 304, continuing the wire guide lumen 308 of the catheter shaft 301 to a point distal of the inflation balloon 304. An expandable stent 312 is positioned about the balloon 304. In an alternative embodiment, an expandable member other than a balloon (e.g., a basket) is disposed near the distal end of the catheter shaft 301. Such an embodiment optionally may have a wire guide through the expandable member. At its proximal end the catheter 300 has a port 310 in fluid communication with the inflation lumen 306. In an alternative embodiment, the port 310 offers access to the guide wire lumen 308. The port 310 may be included in other embodiments, and in other positions on the catheter 300. In another alternative embodiment, the catheter shaft 301 has two ports 310, offering separate access to each of the inflation lumen 306 and the wire guide lumen 308. In other alternative embodiments, the port 310 is useful for introducing another fluid such as a contrast fluid.

Figure 4A:
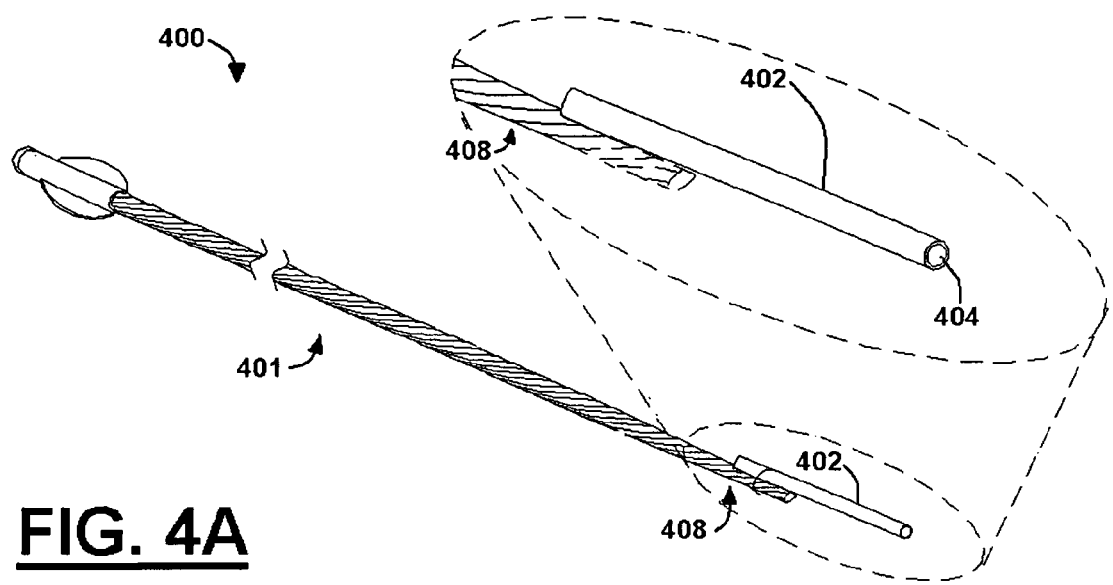
FIG. 4A is a perspective view of a catheter device having an external distal wire guide lumen structure, with an enlarged detail view of the features at the catheter's distal end.
Figure 4B:
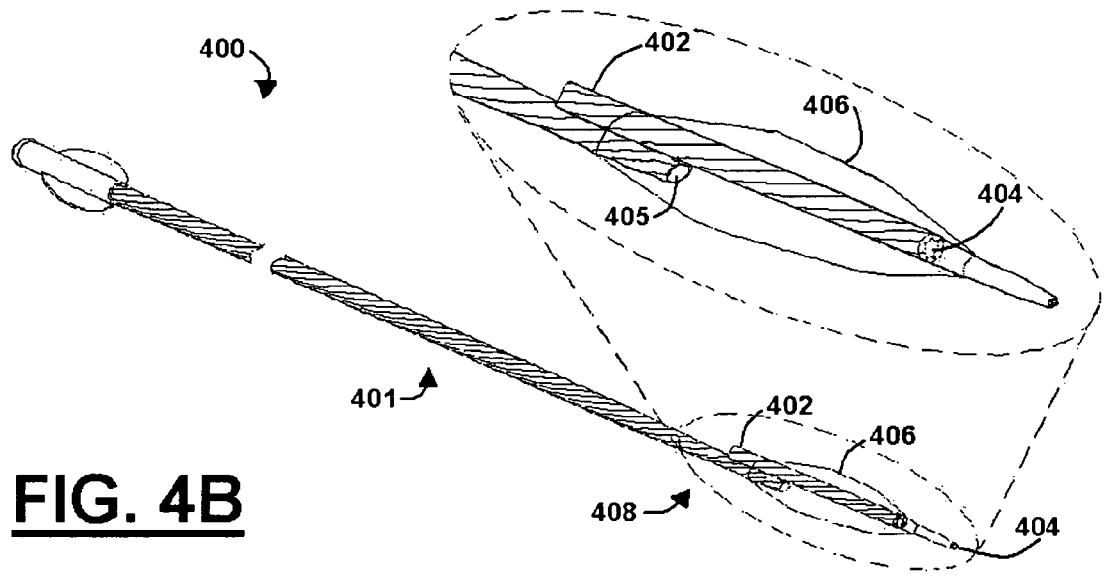
FIG. 4B is a perspective view of a catheter device having an external distal wire guide lumen structure and an inflation balloon, with an enlarged detail view of the features at the catheter's distal end.

FIGS. 4A-4B illustrate embodiments of a multifilar tube balloon catheter device 400 comprising a multifilar shaft 401 and further comprising an external, distally disposed short wire guide lumen structure in the form of a cannula 402 having a wire guide lumen 404 disposed therethrough. In FIG. 4A, the cannula 402 is attached on the distal end 408 of the multifilar catheter shaft 401 using an adhesive. Alternative means of attachment include, for example, forced convection heating, radio frequency heating, ultrasonic welding, and laser bonding. Alternatively, shrink tubing may be used as a manufacturing aid to help compress and fuse the cannula 402 to the multifilar catheter shaft 401. The shrink tubing may be removed and disposed of after the cannula 402 is connected to the catheter shaft 401, or may remain on as part of the connected structure. If the multifilar catheter shaft 401 has a coating, the cannula 402 may be bonded to the coating or directly to the catheter shaft 401. A heat shrink tubing, for example PEBA, may be applied over the entire assembly, which increases the strength of the assembly. In the embodiment shown in FIG. 4B, the cannula 402 is constructed of multifilar tubing. An inflation balloon 406 is mounted on the distal end 408 of the catheter shaft 401. An inflation lumen 405 of the catheter shaft 401 is open to the interior of the inflation balloon 406. The cannula 402 extends through the inflation balloon 406 and has an extension 407 on its distal end. A wire guide lumen 404 runs through the length of the cannula 402 and its extension 407. Although not shown, it should be appreciated that an expandable stent can be disposed about the balloon 406. The cannula 402 providing a wire guide lumen structure can be formed of HDPE, PTFE, PEBA, PET, polyurethane, polyimide, polyolefin, nylon, or any combination thereof. In one embodiment, the cannula 402 comprises a PTFE inner liner and a PEBA outer cover. Other materials may be used as an inner liner such as, for example, HDPE, PET, and polyimide.

Figure 4C:
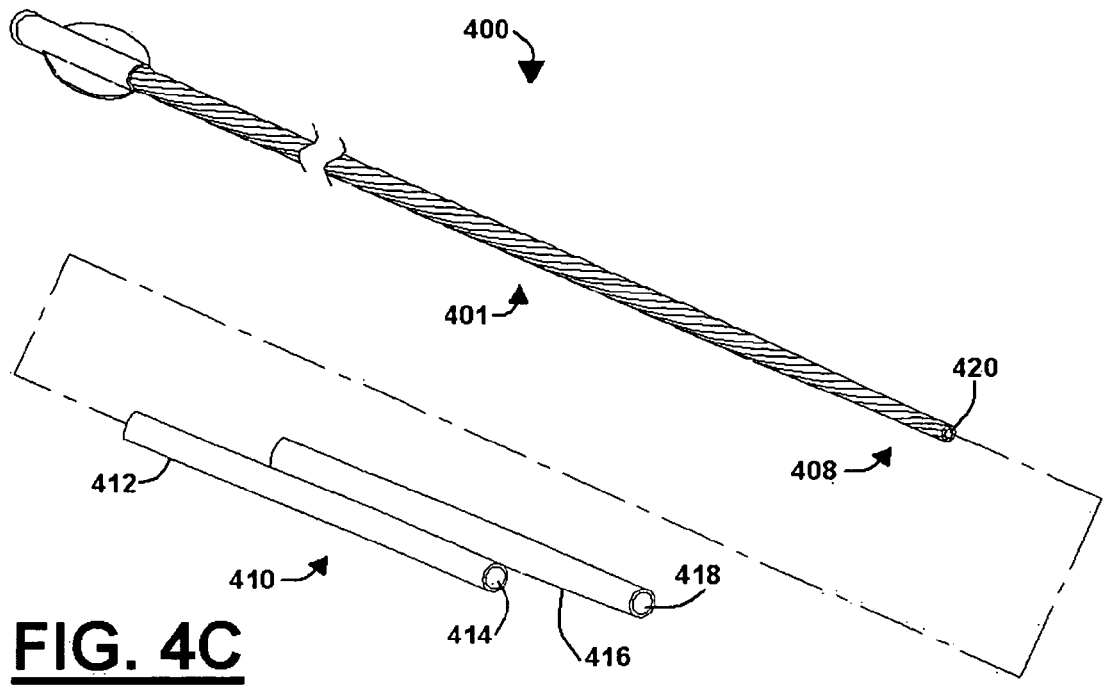
FIG. 4C is a perspective view of a catheter device with a distal dual lumen structure having a wire guide lumen structure and a mounting portion.

In FIG. 4C, a dual lumen structure 410 is disposed on the distal end 408 of the multifilar catheter shaft 401. A portion of the length of dual lumen structure 410 has a "figure 8" cross section. A mounting portion 412 of the dual lumen structure 410 has a lumen 414. The distal end 408 of the catheter shaft 401 fits into the lumen 414. The lumen 414 may be completely occupied by the distal end 408 of the catheter shaft 401, or may continue coaxially beyond the distal end 408 so as to form an extension. If the mounting portion 412 is placed as an extension, the lumen 414 is in fluid communication with a lumen 420 of the shaft 401. A wire guide portion 416 of the dual lumen structure 410 has a wire guide lumen 418 running therethrough. The dual lumen structure 410 is attached on the distal end 408 of the catheter shaft 401 using one of the attachment methods described for the embodiment shown in FIG. 4A. In this embodiment, the lumen 414 of the dual lumen structure is in fluid communication with a lumen 404 of the catheter shaft 401. In an alternative embodiment, a part of the mounting portion 412 is mounted inside the lumen 420 of the catheter shaft 401.

Figure 5A:
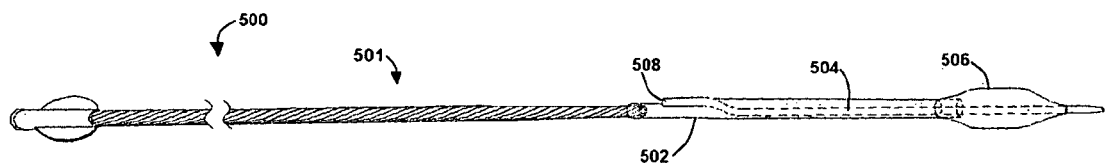
FIGS. 5A-5B show a side view of catheter devices having a distal extension and a wire guide lumen structure.
Figure 5B:
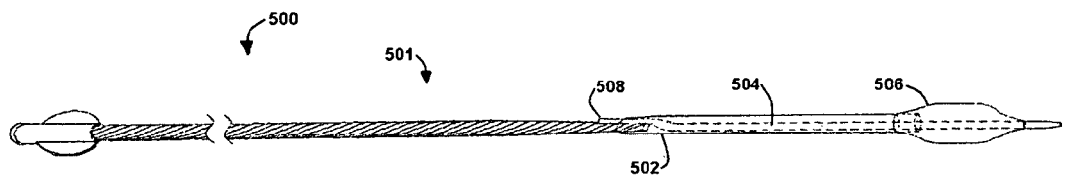
Figure 5C:
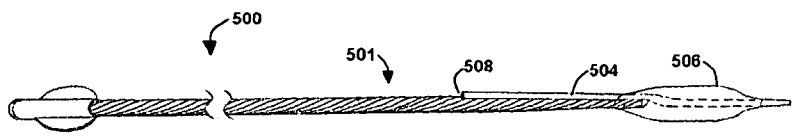
FIG. 5C is a side view of a catheter device having an external distal wire guide lumen structure and an inflation balloon.

FIGS. 5A-5C illustrate embodiments of a balloon catheter 500 incorporating a multifilar shaft 501 and having a short wire guide configuration. The embodiments shown in FIGS. 5A-5B each have a coaxial extension 502 of the multifilar shaft 501, a short wire guide lumen structure in the form of a tube 504, and an inflation balloon 506. The coaxial extension 502 may have the same or a different flexibility than the multifilar shaft 501. In the embodiment illustrated in FIG. 5A, the proximal end 508 of the tube 504 is disposed distal of the juncture of the extension 502 with the multifilar shaft 501. The tube 504 enters the extension 502 and extends through the distal end of the balloon 506. Thus, this embodiment comprises a distal extension of the shaft (in this case the coaxial extension 502) and the wire guide lumen structure 504, a portion of the wire guide lumen structure 504 being coaxial within the distal extension, another portion of the wire guide lumen structure 504 being outside the distal extension adjacent thereto.

In the embodiment illustrated in FIG. 5B, the proximal end 508 of the tube 504 is disposed proximal of the juncture of the extension 502 with the multifilar shaft 501. The tube 504 enters the extension 502 and proceeds through the distal end of the balloon 506. Thus, this embodiment comprises a distal extension of the shaft (in this case the coaxial extension 502) and the wire guide lumen structure 504, a portion of the wire guide lumen structure being coaxial within the distal extension, another portion of the wire guide lumen structure 504 being outside the shaft adjacent thereto. The embodiment illustrated in FIG. 5C does not have an extension. The balloon 506 is disposed on the distal end of the multifilar shaft 501. The proximal end 508 of the tube 504 is disposed proximal of the juncture of the extension 502 with the multifilar shaft 501 and is affixed to the exterior of the multifilar shaft 501. The tube 504 passes through the middle of the balloon 506 and proceeds through the distal end of the balloon 506. In each of the embodiments shown in FIGS. 5A-5C, the placement of the proximal end 508 of the tube 504 along the multifilar shaft 501 affects the flexibility of the shaft 501. Therefore, variation in the placement is useful in increasing or reducing flexibility as desired in other embodiments.

Figure 6C:
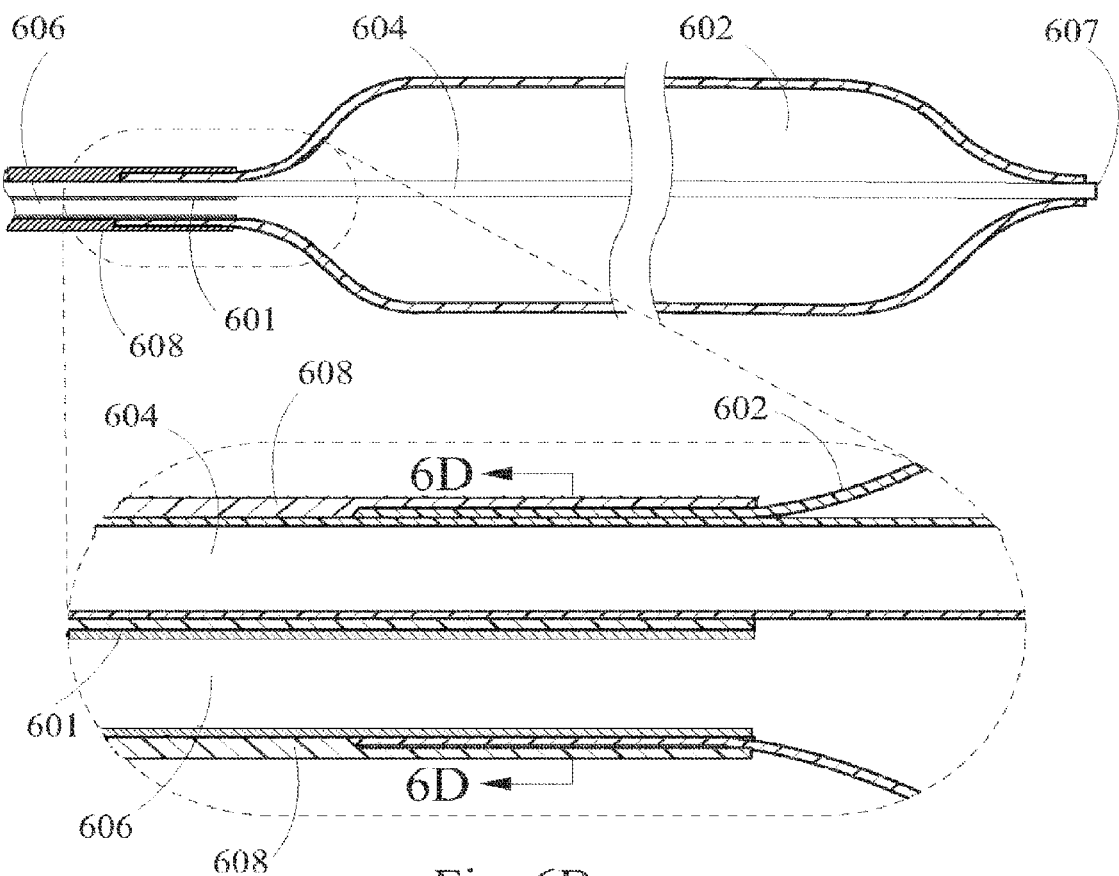
FIG. 6C is a transverse cross-sectional view of a dual-lumen mounting sleeve.
Figure 6C:
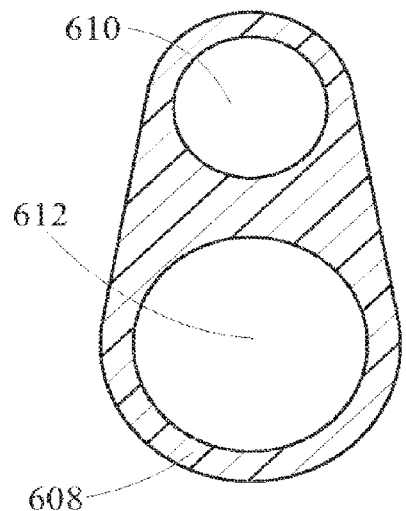

FIG. 6 illustrates one embodiment of a balloon catheter 600 having an elongate shaft 601 comprising a multifilar tube. An inflation balloon 602 is disposed near the distal end. FIG. 6A is an enlarged detail illustration of a middle section of the catheter 600. As can be clearly seen in FIG. 6A, the shaft 601 includes an external wire guide lumen 604 and an internal inflation lumen 606. As shown in FIG. 6A, this embodiment the catheter shaft 601 is coated with a PEBA coating 603. The coating 603 serves to reduce friction during introduction of the catheter shaft 601 and provides a seal to prevent leakage of inflation fluid from the inflation lumen 606 through the walls of the shaft 601. As can also be seen in FIG. 6A, the catheter shaft 601 tapers distally to a smaller diameter along the region 605.

Figure 6D:
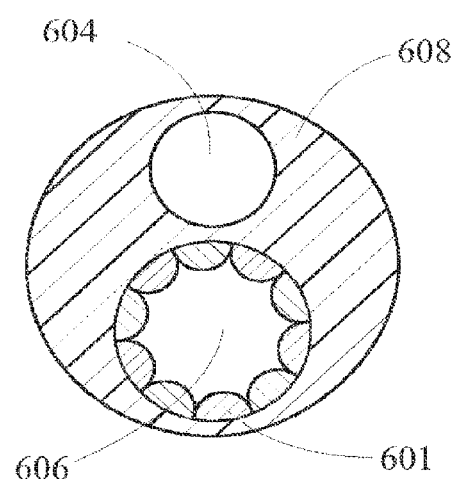
FIG. 6D is a transverse cross-sectional view along line 6D-6D of FIG. 6B showing two lumens of the catheter device surrounded by a mounting sleeve.

FIG. 6B is an enlarged detail illustration of a distal section of the balloon catheter 600. As shown in FIG. 6B, the inflation lumen 606 opens into the inflation balloon 602, and the wire guide lumen 604 extends through the balloon 602 to the distal end 607. FIG. 6B includes an enlarged detail portion more clearly illustrating the relationship between the balloon 602 and the two lumens (604 and 606). In this embodiment, the balloon 602 and wire guide lumen 604 are mounted to the shaft 601 with a PEBA shrink sleeve 608. As shown in FIG. 6C, a cross-sectional view of the sleeve 608 has approximately a figure-eight shape before mounting. The sleeve 608 has two central apertures (610 and 612) to allow mounting the sleeve 608 over the wire guide lumen 604 and the shaft. In this embodiment, after the balloon 602 and wire guide 604 are assembled to the shaft 601 together with the sleeve 608, the sleeve 608 is heated to shrink and form to the assembly of shaft 601, balloon 602, and wire guide 604. FIG. 6D is a transverse cross section along line 6D-6D of FIG. 6B, and shows the finished configuration. The sleeve 608 forms to the shaft 601 and leaves open the inflation lumen 606 and the wire guide lumen 604. As is clearly shown with reference to the longitudinal section view of FIG. 6A and the transverse section view of FIG. 6D, the multifilar tubing shaft 601 is formed as a continuous monolayer of laterally-touching coiled filars, each having a length that does not cross over itself nor other filars, which monolayer may be covered with a coating material.

Cross-lumen communication may be prevented. For example, the walls of the multifilar tube of the elongate shaft 601 may be porous, and pressure exerted on an inflation fluid in the inflation lumen 606 may urge inflation fluid into the wire guide lumen 604. According to one aspect, this may be prevented by lining the wire guide lumen 604 with a liner such as, for example, PTFE, although other materials may be used. Furthermore, as shown in FIG. 9 an inner coating segment 609 may be placed over the elongate shaft 601 beneath the proximal breach or side opening of the wire guide lumen 604. The inner coating segment may be, for example, PEBA. The inner coating segment may be implemented to alter flexibility in the area of the segment, for example to avoid abrupt changes in flexibility. In the embodiment of FIG. 9, the proximal end of the segment 609 terminates at about halfway through the taper 605 and the distal end of the segment terminates just distal of the proximal breach or side opening of the wire guide lumen 604. According to another aspect, cross-lumen communication may be prevented by placing the coating 603 over essentially the entire length of the elongate shaft 601, and the sleeve 608 may subsequently be placed over the coating 603 and elongate shaft 601. According to yet another aspect, cross-lumen communication may be prevented by simply making the walls of the sleeve 608 thicker. A 0.001 inch (0.025 mm) wall thickness of the coating 603 or sleeve 608, for example, may be sufficient. As mentioned previously, the coating 603 and sleeve 608 may be PEBA. These principles may be implemented in other embodiments of the invention as may be desirable due to fluid being passed through or injected into one of the lumens.

Figure 7A:
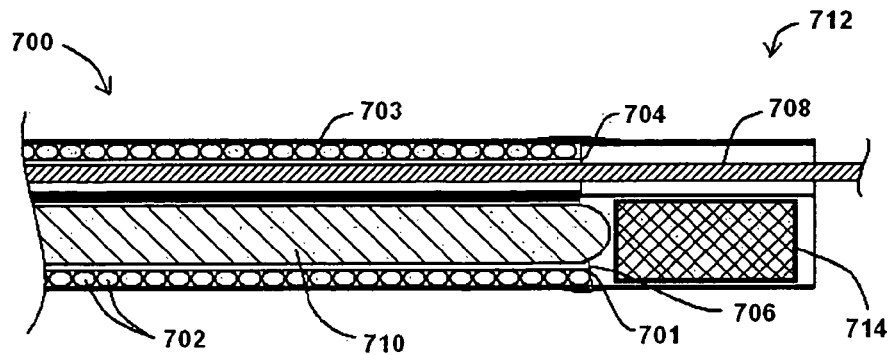
FIGS. 7A and 7B illustrate a cross-sectional view of another embodiment of a catheter device
Figure 7B:
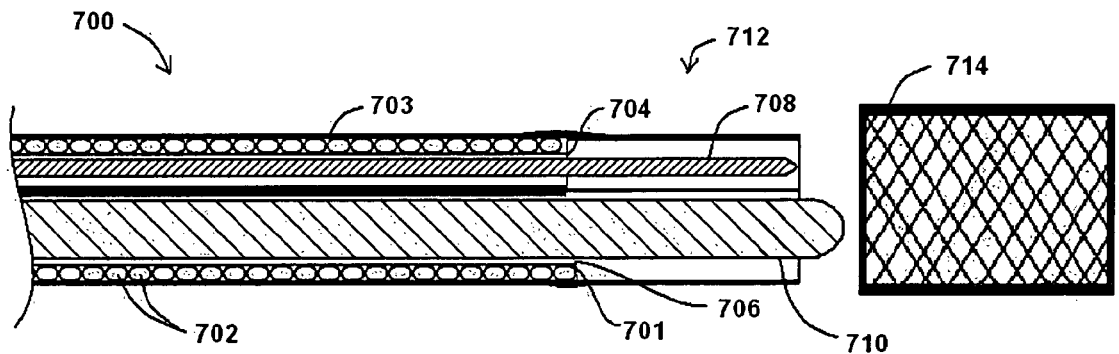

FIGS. 7A-7B illustrate a cross-sectional view of a portion of a catheter device 700 according to one aspect of the present invention. A shaft wall comprising multiple filars 702 includes an inner coating 701 and an outer coating 703, and surrounds a first lumen 704 and a second lumen 706. A wire guide 708 extends through the first lumen 702, and a stent-deployment shaft 710 extends through the second lumen 706. As shown in FIG. 7A, the catheter device 700 includes a distal extension 712 that houses a self-expandable stent 714. FIG. 7B illustrates the stent 714 having been pushed out of the second lumen 706 by the stent-deployment shaft 710 such that the stent 714 is deployed. Prior to deployment of the stent 714, the wire guide 708 is typically retracted into the shaft wall or lumen 704 so as not to interfere with deployment of the stent 714.

Figure 8:
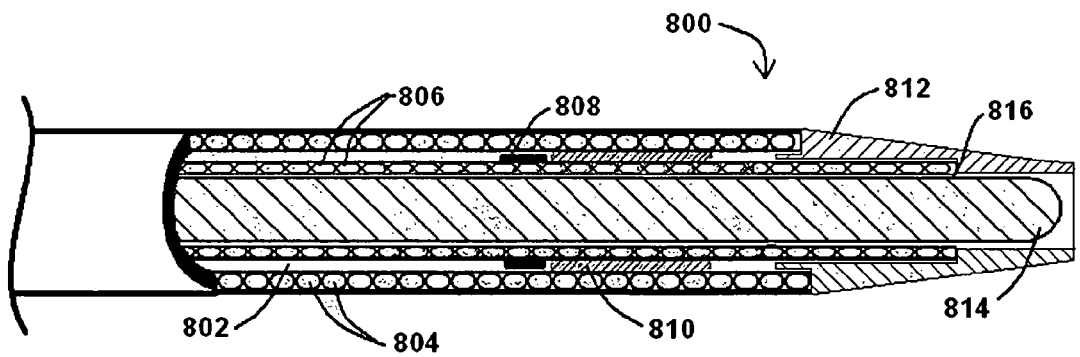
FIG. 8 illustrates a partial cross-sectional view of yet another embodiment of a catheter device.

FIG. 8 illustrates a partial cross-sectional view of another embodiment of a catheter device 800, including a self-expanding stent 810. The catheter device 800 has a central lumen 802 surrounded by a first, outer tubular multifilar body 804. A second, inner multifilar cable tube is coaxially disposed in the central lumen 802 for use as a pusher 806. The pusher 806 has a protruding engagement surface 808 for pushing the self-expanding stent 810 out of the central lumen 802 or for holding the stent 810 as the outer tubular multifilar body 804 is being pulled in a proximal direction. A tapered tip 12 is mounted on the distal end of the pusher 806, and provides a minimally traumatic leading surface for the catheter device 800. A wire guide 814 extends through a central wire guide lumen 816 of the pusher 806. Optionally, apertures (not shown) may be provided through the side of the outer tubular body 804 and the pusher 806 to permit the wire guide 814 to exit the central lumen 802 and the wire guide lumen 816 at an intermediate location. The self-expanding stent 810 is adapted to be deployed when a user retracts the outer tubular body 804 proximally while holding the pusher 806 substantially in place. The protruding engagement surface 808 of the pusher 806 holds the self-expanding stent 810 substantially in place while the outer tubular body 804 is withdrawn from around it. Once the stent 810 is deployed, the pusher 806 and wire guide 814 are withdrawn, leaving the stent 810 in the position where it was deployed.

In alternative embodiments, the shaft coating (if any) may be a material other than PEBA, and may be the same or different than the material in a mounting sleeve used to mount a balloon (for example, HDPE, PTFE, PET, polyurethane, polyimide, polyolefin, nylon, or any combination thereof). In other alternative embodiments, the multifilar catheter shaft need not have a lumen running through its length, but may be relatively solid (e.g., for use as a pushing tool, or for use in a configuration not requiring a lumen through the catheter shaft). The balloon catheters of the present invention are adaptable for use with expandable stents as is illustrated, for example, in FIG. 3B.

It is therefore intended that the foregoing detailed description be regarded as illustrative rather than limiting, and that it be understood that it is the following claims, including all equivalents, that are intended to define the spirit and scope of this invention.

I claim:

1. A catheter device, comprising:
    an elongate catheter shaft comprising
    a monolayer multifilar tubing having a proximal portion and a tapered distal portion, the tubing defining a first tubing lumen;
    a polymeric coating covering at least a portion of the tubing;
    an expandable balloon including an expandable balloon lumen;
    a wire guide lumen formed in a dual-lumen sleeve attached near the distal end of the distal portion and wherein the wire guide lumen is disposed wholly external of, with its entire adjacent length being parallel to the multifilar tubing; and
    an inner coating segment covering a length of the tubing and disposed between the tubing and the wire guide lumen, where the inner coating segment extends from a terminus at about halfway through said tapered distal portion to a terminus just distal of an opening defining a proximal end of the wire guide lumen;
    wherein at least a part of the distal tubing portion is more flexible than the proximal portion;
    wherein the multifilar tubing terminates within the balloon lumen such that the first tubing lumen is in fluid communication with the balloon lumen; and the wire guide lumen extends through the balloon lumen, providing a patent path to a distal end of the balloon.

2. The catheter device of claim 1, wherein the balloon comprises the same polymer as the coating.

3. The catheter device of claim 1, further comprising a deployable stent disposed about the expandable balloon.

4. The catheter device of claim 1, further comprising a self-expanding stent.

5. The catheter device of claim 1, wherein said wire guide lumen comprises a liner configured to prevent cross-lumen communication of an inflation fluid between the first tubing lumen and the wire guide lumen.

* * * * *

UNITED STATES PATENT AND TRADEMARK OFFICE
CERTIFICATE OF CORRECTION

| | | |
|---|---|---|
| PATENT NO. | : 7,959,660 B2 | Page 1 of 1 |
| APPLICATION NO. | : 11/300635 | |
| DATED | : June 14, 2011 | |
| INVENTOR(S) | : Lentz | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 328 days.

Signed and Sealed this
Ninth Day of August, 2011

David J. Kappos
*Director of the United States Patent and Trademark Office*